United States Patent [19]
Janchitraponvej et al.

[11] Patent Number: 5,756,080
[45] Date of Patent: *May 26, 1998

[54] STABLE CONDITIONING SHAMPOO HAVING A HIGH FOAM LEVEL CONTAINING A GRAFT COPOLYMER OF POLYETHYLENIMINE AND SILICONE AS A CONDITIONER

[75] Inventors: Ben Janchitraponvej, Niles; William Brown, Flossmoor, both of Ill.

[73] Assignee: Helene Curtis, Inc., Chicago, Ill.

[*] Notice: The term of this patent shall not extend beyond the expiration date of Pat. No. 5,556,616.

[21] Appl. No.: 600,746

[22] Filed: Feb. 13, 1996

Related U.S. Application Data

[63] Continuation-in-part of Ser. No. 298,944, Aug. 31, 1994, Pat. No. 5,556,616, which is a continuation-in-part of Ser. No. 62,606, May 17, 1993, Pat. No. 5,417,965, which is a continuation-in-part of Ser. No. 719,818, Jun. 24, 1991, Pat. No. 5,221,530.

[51] Int. Cl.$^6$ .................................................. A61K 7/075
[52] U.S. Cl. ........................... 424/70.122; 424/70.11; 424/70.12
[58] Field of Search ................... 424/70.122, 70.11, 424/70.12, 70.1

[56] References Cited

U.S. PATENT DOCUMENTS

| | | | |
|---|---|---|---|
| 3,761,417 | 9/1973 | Parran | 252/106 |
| 4,140,759 | 2/1979 | Mausner | 424/70 |
| 4,252,656 | 2/1981 | Liebowitz et al. | 252/8.8 |
| 4,311,626 | 1/1982 | Ona et al. | 524/500 |
| 4,344,763 | 8/1982 | Tolgyesi et al. | 8/127.51 |
| 4,381,259 | 4/1983 | Homma et al. | 252/542 |
| 4,402,977 | 9/1983 | Grollier et al. | 424/70 |
| 4,559,227 | 12/1985 | Chandra et al. | 424/70.122 |
| 4,586,518 | 5/1986 | Cornwall et al. | 132/206 |
| 4,591,610 | 5/1986 | Grollier | 424/70 X |
| 4,657,690 | 4/1987 | Grollier et al. | 424/70 X |
| 4,663,158 | 5/1987 | Wolfram et al. | 424/174.15 |
| 4,728,457 | 3/1988 | Fieler et al. | 252/174.15 |
| 4,741,855 | 5/1988 | Grote et al. | 252/142 |
| 4,749,732 | 6/1988 | Kohl et al. | 525/43 |
| 4,842,851 | 6/1989 | Grollier et al. | 424/70 |
| 4,940,576 | 7/1990 | Walsh | 424/70 |
| 4,983,383 | 1/1991 | Maksimoski et al. | 424/70 |
| 5,034,218 | 7/1991 | Duvel | 424/70 |
| 5,037,818 | 8/1991 | Sime | 514/183 |
| 5,085,857 | 2/1992 | Reid et al. | 424/70 |
| 5,100,660 | 3/1992 | Hawe et al. | 424/78.35 |
| 5,104,645 | 4/1992 | Carden et al. | 424/70 |
| 5,118,498 | 6/1992 | Helioff et al. | 424/70.11 |
| 5,183,601 | 2/1993 | Jisai et al. | 252/524 |
| 5,556,616 | 9/1996 | Janchitraaponvej et al. | 424/70.122 |

FOREIGN PATENT DOCUMENTS

| | | |
|---|---|---|
| 0093601 | 11/1983 | European Pat. Off. . |
| 479 000 A2 | 4/1992 | European Pat. Off. . |
| 2-59510 | 2/1990 | Japan . |

OTHER PUBLICATIONS

CTFA Cosmetic Ingredient Handbook (First Edition) published by The Cosmetic, Toiletry and Fragrance Association, Inc., Copyright ©1988, pp. 56–58, 71–73, and 319.
Petrarch Systems product/pricing publication.
Leaflet of Allied Collids, Inc., which is intended for general guidance in the use of their products.
Leaflet of Allied Collids, Inc., entitled "Current Status of Salcare SC92 Product."

*Primary Examiner*—Robert H. Harrison
*Attorney, Agent, or Firm*—Matthew Boxer

[57] ABSTRACT

A conditioning shampoo containing an anionic cleansing surfactant, in an amount of about 5% to about 65% by weight, preferably about 5% to about 25% by weight, e.g., an ethoxylated ($C_{12}$–$C_{22}$) alkyl sulfate and/or a long chain ($C_{12}$–$C_{22}$) alkyl sulfonate, and a graft copolymer of a polyethylenimine and a silicone polymer in an amount of about 0.1% to about 20% by weight, preferably about 0.1% to about 10% by weight, is disclosed. The composition provides excellent foaming, conditioning, and phase stability.

34 Claims, No Drawings

5,756,080

STABLE CONDITIONING SHAMPOO HAVING A HIGH FOAM LEVEL CONTAINING A GRAFT COPOLYMER OF POLYETHYLENIMINE AND SILICONE AS A CONDITIONER

CROSS REFERENCE TO RELATED APPLICATION

This application is a continuation-in-part of application U.S. Ser. No. 08/298,944 filed Aug. 31, 1994, now U.S. Pat. No. 5,556,616, which is a continuation-in-part of U.S. Ser. No. 08/062,606 filed May 17, 1993, now U.S. Pat. No. 5,417,965 issued May 23, 1995, which is a continuation-in-part of U.S. Ser. No. 07/719,818 filed Jun. 24, 1991, now U.S. Pat. No. 5,221,530 issued Jun. 22, 1993.

FIELD OF THE INVENTION

The present invention is directed to a hair conditioning shampoo composition and to a method of treating hair with the composition to provide the hair with improved wet stage and dry stage conditioning properties, as well as other conditioning properties, such as softness, without residual build-up of conditioning agents on the hair. The conditioning shampoo also thoroughly cleanses the hair, while conditioning, with a cleansing detergent that develops an unexpectedly high foam level and has unexpected stability. The conditioning shampoo contains an anionic detergent, and a conditioner that is a graft copolymer of a polyethylenimine (PEI) and a silicone polymer, e.g., a dimethylpolysiloxane. More particularly, the present invention is directed to a hair conditioning shampoo composition including one or more anionic cleansing surfactants, such as ammonium lauryl sulfate (ALS) or ammonium lauryl ether sulfate (ALES), and a PEI-silicone graft copolymer conditioner, that is stable over extended periods of time at elevated temperatures.

Surprisingly, the composition develops copious amounts of foam for a conditioning shampoo while achieving excellent conditioning benefits; is unexpectedly stable without requiring suspending agents normally required to suspend silicone conditioning agents; and provides excellent foaming and cleansing using a smaller amount of strong anionic cleansing detergents, such as a long chain alkyl sulfate, or an ethoxylated long chain alkyl sulfate or sulfonate, e.g., about 5% to about 15% vs. about 18% to about 21% active anionic surfactants used in prior art shampoos containing a silicone conditioning agent.

BACKGROUND OF THE INVENTION AND PRIOR ART

Soiled human hair is shampooed to remove sebum that is naturally secreted by the head, as well as soil and other atmospheric contaminants that accumulate on the hair. Sebum, in particular, accumulates on the hair in a relatively short period of time leaving the hair with a greasy, dirty feel and poor manageability. The most effective shampoos for cleansing the hair of the atmospheric contaminants and sebum are those that contain high lather synthetic anionic detergents, such as the long chain alkyl sulfates, the ethoxylated long chain alkyl sulfates, and the long chain sulfonates. These synthetic anionic detergents are very effective for cleansing the hair, but, after rinsing with water, leave the hair with a dried touch, usually called "creak," and result in hair, when wet, that is in an extremely tangled and unmanageable after-shampoo condition.

Thoroughly cleansed hair is extremely difficult to comb, in either the wet or dry state, because the individual hair fibers tend to snarl, kink, and interlock with each other. In this after-shampoo stage, particularly prior to complete drying of thoroughly cleansed hair, the hair is very difficult to comb or brush. Even after complete drying, the thoroughly cleansed hair remains difficult to comb or brush and does not set well. Thoroughly cleaned and dried hair also has undesirable electrostatic properties in a low humidity atmosphere that causes the hair to "fly away," thereby further reducing the combing or brushing property of the hair. Generally, these above-outlined problems that result from synthetic detergent cleansing of the hair, particularly for the high-lather synthetic anionic detergents, have been alleviated either by the after-shampoo treatment of the hair with hair conditioners, for example, in the form of a hair rinse, or by including hair conditioners directly within the shampoo composition.

After-shampoo hair conditioning compositions are easily formulated, but are inconvenient to use because of the necessity of applying the conditioner to the hair in a separate stage, after shampooing. The preparation of a conditioning shampoo has been more difficult because of inherent incompatibility problems between anionic surfactants and the cationic compounds that are good conditioning agents. Contact between an anionic surfactant and a cationic surfactant or cationic polymer produces a precipitate that forms immediately or causes an interaction between the anionic and cationic components that significantly reduces their respective cleaning and conditioning properties, and especially a very noticeable and severe loss of foam attributed to the anionic cleansing surfactant. The reduction in cleansing and conditioning effectiveness is observed even in compositions wherein the anionic and cationic components do not precipitate from the composition but remain in solution or suspension. This incompatibility between anionic surfactants and cationic conditioning components is well recognized by those skilled in the art. For example, Sagarin in *Cosmetics*, Interscience Publishers, Inc., New York, p. 538 (1957), states that anionic and cationic compounds cannot be used in combination because they react to form insoluble salts.

A partial solution to this incompatibility problem in the formulation of conditioning shampoos is exemplified by the following patents that disclose compositions that contain surfactants that are not anionic, e.g., nonionics, amphoterics and zwitterionics, together with cationic conditioning compounds: U.S. Pat. No. 3,849,348 to Hewitt; U.S. Pat. No. 3,990,991 to Gerstein; and U.S. Pat. No. 3,822,312 to Sato.

Another problem inherent in formulating a conditioning shampoo is an instability problem that results when water-insoluble conditioning agents also are included in the conditioning shampoo composition, such as the nonvolatile silicones that are well recognized in the art as providing a degree of softness to the hair.

Silicones in shampoo compositions have been disclosed in a number of different patents: U.S. Pat. No. 2,826,551, Mar. 11, 1958 to Green; U.S. Pat. No. 3,964,500, Jun. 22, 1976 to Drakoff; U.S. Pat. No. 4,364,837, Dec. 21, 1982 to Pader; British Patent No. 849,433, Sep. 28, 1960 to Woolston; U.S. Pat. No. 4,741,855 to Grote et al.; U.S. Pat. Nos. 4,788,006 and 4,902,499 to Bolich, Jr. et al.; U.S. Pat. No. 4,704,272 to Oh et al.; and Janchitraponvej U.S. Pat. Nos. 4,954,335 and 5,328,685. The silicones are well known to substantially reduce the foaming of anionic cleansing surfactants.

A particularly difficult problem to solve in silicone-containing conditioning shampoos is that of providing a conditioning shampoo that provides excellent cleansing of the hair while providing high foaming and, at the same time, also has excellent conditioning performance.

Polyethylenimine (PEI) is disclosed as a separate component for a conditioning shampoo in the parent application (now U.S. Pat. No. 5,221,530). PEI provides excellent wet combing benefits, but does not significantly improve dry combing. While the addition of a silicone fluid and/or silicone gum to a conditioning shampoo improves dry feel, the silicones require the use of a suspending agent, and also lower the amount of foam generated during shampooing.

Compositions of the present invention are capable of providing excellent conditioning, cleansing, and foam levels by incorporating a conditioning agent that is a graft copolymer of polyethylenimine and a silicone polymer into a shampoo formulation.

SUMMARY OF THE INVENTION

In brief, the present invention is directed to a method and composition for simultaneously shampooing and conditioning hair, while maintaining foam, that includes an aqueous carrier; an anionic cleansing surfactant, such as an alkyl sulfate or an alkyl ether sulfate, in an amount of about 5% to about 65% by total weight of the composition; and a polyethylenimine-silicone graft copolymer as a conditioning agent and in an amount of about 0.01% to about 20% by total weight of the composition.

As used herein, the term "graft copolymer" is defined as a copolymer having a backbone chain to which side chains of a different chemical composition are attached at various positions along the backbone. The term "graft copolymer," therefore, includes block copolymers in which polymeric units, i.e., blocks, are the pendant moieties on backbone chain of different chemical composition.

The composition has extended product stability, excellent overall conditioning to human hair, particularly superior wet and dry combing properties, and unexpectedly maintains very high levels of foam.

It was further surprisingly and unexpectedly found that hair treated with the compositions of the present invention is thoroughly cleansed at high foam levels and exhibits improved physical and cosmetic properties, such as gloss, wet combing, dry combing, thickness, manageability, softness and body.

Therefore, one aspect of the present invention is to provide a hair-treating composition that cleanses the hair and imparts improved physical properties and cosmetic properties to the hair in a single application of a mild conditioning shampoo that generates unexpectedly high foam quantities.

Another aspect of the present invention is to provide a physically stable conditioning shampoo containing an anionic surfactant, and a graft copolymer of a polyethylenimine (PEI) and a silicone polymer, that provides hair conditioning and composition stability, wherein the composition generates excellent foam levels and can be formulated at room temperature.

Another aspect of the present invention is to provide a new and improved conditioning shampoo containing a strong anionic detergent, such as a long chain alkyl sulfate, long chain alkyl ether sulfate, and/or long chain sulfonate, that is compatible with cationic conditioning agents, and that maintains an unexpectedly high foam level although the composition contains a PEI-silicone graft copolymer conditioning agent.

Still another aspect of the present invention is to provide a new and improved conditioning shampoo including, by total weight of the composition, (a) about 5% to about 25% of an anionic surfactant, (b) about 0.01% to about 20%, preferably about 0.05% to about 10%, most preferably about 0.5% to about 10%, of a polyethylenimine-silicone graft copolymer that surprisingly provides composition stability and conditioning benefits, particularly increased wet and dry combing and reduced static (fly away) for better manageability, and (c) optionally, any known emulsion stabilizer and/or a viscosity increasing agent for added stability of aqueous emulsions, each in an amount of about 0% to about 10% by total weight of the composition, and preferably about 0.1% to about 5% by weight.

A further aspect of the present invention is to provide a new and improved method of cleansing and conditioning hair, simultaneously, with a composition containing one or more anionic surfactants; and a polyethylenimine-silicone graft copolymer conditioning agent, while providing high foam levels, and excellent cleansing, excellent conditioning in a stable conditioning shampoo.

Still another aspect of the present invention is to provide a new and improved conditioning shampoo having a pH of about 4 to about 10, including about 5% to about 65% of an anionic surfactant; and a polyethylenimine-silicone graft copolymer in an amount of about 0.01% to about 20%, by total weight of the composition.

Another object of the present invention is to provide a new and improved conditioning shampoo having a pH of about 5 to about 7, including about 5% to about 15% of an anionic surfactant; and a graft copolymer of a polyethylenimine and a silicone polymer, in an amount of about 0.05% to about 10%, by total weight of the composition.

The above and other aspects and advantages of the present invention will become apparent from the following detailed description of the preferred embodiments.

DETAILED DESCRIPTION OF THE PREFERRED EMBODIMENTS

The aqueous conditioning shampoo compositions of the present invention generally include water in an amount of about 10% to about 80–90% by total weight of the composition; an anionic surfactant, preferably in an amount of about 5% to about 65%, and preferably about 5% to to about 25%, by total weight of the composition; and a graft copolymer of a polyethylenimine and a silicone polymer, preferably an organosiloxane, such as a dimethylpolysiloxane, in an amount of about 0.01% to about 20%, preferably about 0.05% to about 10%, by total weight of the composition.

The conditioning shampoo of the present invention provides the hair with improved physical and cosmetic conditioning properties, such as gloss, thickness, softness, and manageability, including excellent wet and dry combing properties and body, simultaneously with excellent cleansing at high foam levels in a mild conditioning shampoo. As will be demonstrated more fully hereinafter, it is surprising and unexpected that the composition of the present invention, including an anionic cleansing detergent and a cationic PEI-silicone graft copolymer conditioning agent, is able to provide excellent cleansing at a high foam level in a stable composition containing a silicone conditioning agent.

The anionic cleansing surfactant used in the composition and method of the present invention can be any of the anionic surfactants known or previously used in the art of hair shampoos. An anionic cleansing surfactant should be included in the composition of the present invention to effectively cleanse the hair and generate a high, stable foam level that consumers equate with cleaning efficiency. While nonionic and amphoteric surfactants have not been as effective in cleansing the hair and do not provide the high foam level desired by consumers, surprisingly, it has been found that the composition of the present invention provides excellent foam levels with the less strong anionic cleansing detergents or with the strong anionic detergents at levels generally below about 15%, i.e., about 5% to about 15%, by total weight of the composition, particularly when the foam level is boosted with one or more common foam boosters, such as a betaine or other foam booster. Optionally, nonionic, amphoteric, and/or zwitterionic surfactants can be included in the compositions of the present invention, in addition to one or more anionic surfactants, to help stabilize foam, to provide a suitable viscosity, or to give other functional or esthetic properties to the composition.

Usually, the anionic cleansing surfactant includes a hydrophobic moiety, such as a carbon chain having from about eight carbon atoms to about 30 carbon atoms, and particularly from about 12 carbon atoms to about 22 carbon atoms, and further includes a hydrophilic moiety, such as a sulfate, sulfonate, carbonate, phosphate or carboxylate. Often, the hydrophobic carbon chain is etherified, such as with ethylene oxide or propylene oxide, to impart a particular physical property, such as increased water-solubility or reduced surface tension, to the anionic cleansing surfactant.

Suitable anionic cleansing surfactants include, but are not limited to, compounds in the classes known as alkyl sulfates, alkyl ether sulfates, alkyl sulfonates, alkyl ether sulfonates, sulfate esters of an alkylphenoxy polyoxyethylene ethanol, alpha-olefin sulfonates, beta alkyloxy alkene sulfonates, alkyl arylsulfonates, alkyl carbonates, alkyl ether carboxylates, fatty acids, succinamates, sulfosuccinates, sarcosinates, octoxynol or nonoxynol phosphates, taurates, fatty taurides, sulfated monoglycerides, fatty acid amino polyoxyethylene sulfates and isothienates; or combinations thereof. Many additional anionic cleansing surfactants are described in McCUTCHEON'S DETERGENTS AND EMULSIFIERS, 1989 ANNUAL published by McCutcheon's Division MC Publishing Company, herein incorporated by reference. Usually, the anionic cleansing surfactant is present in the composition as a neutralized salt in the form of a sodium, potassium, lithium, ammonium, alkylammonium, or hydroxyalkylammonium salt, wherein the alkyl moiety has one to about three carbon atoms.

Exemplary anionic cleansing surfactants that are useful in the composition and method of the present invention include, but are not limited to, the ammonium, monoethanolamine, diethanolamine, triethanolamine, isopropylamine, sodium, potassium, lithium, or magnesium salts of lauryl sulfate, dodecylbenzenesulfonate, lauryl sulfosuccinate, lauryl ether sulfate, lauryl ether carboxylate, lauryl sarcosinate, cocomethyl tauride, and sulfosuccinate half ester amide; or combinations thereof.

Also useful are the anionic carboxylate cleansing detergents, such as $C_{11}$–$C_{15}$ Pareth-7 carboxylic acid, $C_{11}$–$C_{15}$ Pareth-9, $C_{11}$–$C_{15}$ Pareth-12, $C_{11}$–C15 Pareth-20, $C_{11}$–$C_{15}$ Pareth-30, $C_{11}$–$C_{15}$ Pareth-40, $C_{11}$–$C_{21}$ Pareth-10, $C_{12}$–$C_{13}$ Pareth-5 carboxylic acid, $C_{12}$–C15 Pareth-2 phosphate, $C_{12}$–$C_{15}$ Pareth-7 carboxylic acid, $C_{12}$–$C_{15}$ Pareth-9, $C_{12}$–$C_{15}$ Pareth-12, $C_{14}$–$C_{15}$ Pareth-13, $C_{22}$–$C_{24}$ Pareth-33, cocaminobutyric acid, cocaminopropionic acid, coceth-7 carboxylic acid, cocoamphodipropionic acid, coconut acid, deceth-7 carboxylic acid, hydrogenated coconut acid, hydrogenated menhaden acid, hydrogenated tallow acid, hydroxystearic acid, isostearic acid, lanolin acid, lauraminopropionic acid, laureth-5 carboxylic acid, laureth-10 carboxylic acid, lauroamphodipropionic acid, linoleic acid, linolenic acid, linseed acid, MEA-laureth-6-carboxylate, myristaminopropionic acid, palmitic acid, sodium $C_{12}$–$C_{15}$ Pareth-6 carboxylate, sodium $C_{12}$–$C_{15}$ Pareth-7 carboxylate, sodium ceteth-13 carboxylate, sodium isosteareth-6 carboxylate, sodium isosteareth-11 carboxylate, sodium laureth-13 carboxylate, sodium trideceth-7 carboxylate, sodium trideceth-12 carboxylate, trideceth-4 carboxylic acid, trideceth-7 carboxylate acid, trideceth-15 carboxylic acid, and trideceth-19 carboxylic acid.

The following low-irritation surfactants are particularly useful in formulating a "baby" shampoo having high performance in terms of foam level and cleansing while achieving exceptional mildness:

ANIONICS:
Disodium Laureth Sulfosuccinate;
Disodium Lauroamido MEA Sulfosuccinate;
Disodium Ricinoleamido MEA Sulfosuccinate;
Ceteareth-25-Carboxylic Acid;
Trideceth-7-Carboxylic Acid;
Pareth-25-6-Carboxylic Acid;
Trideceth-4-Carboxylic Acid;
Trideceth-19-Carboxylic Acid;
Sodium Trideceth-12-Carboxylate;
Sodium Ceteth-13-Carboxylate;
Laureth-5-Carboxylic Acid (SANDOPAN® LA8);
Sodium Laureth-13-Carboxylate;
Sodium Oleth-13-Carboxylate;
Sodium Ceteareth-5-Carboxylate;
Sodium Ceteareth-9-Carboxylate;
Isosteareth-6-Carboxylic Acid; and
Isosteareth-11-Carboxylic Acid.

NONIONICS:
PEG 30 Glyceryl Mono Cocoate;
PEG 78 Glyceryl Mono Cocoate;
PEG 82 Glyceryl Mono Tallowate;
PEG 200 Glyceryl Mono Tallowate; and
PEG 20 Glyceryl Mono Tallowate.

AMPHOTERICS:
Cocampho-Carboxyglycinate (VARION® 2C);
Lauroampho-Carboxyglycinate (VARION® 2L);
Cocamidopropyl Betaine; and
Cocamidopropyl Hydroxysultaine (VARION® CAS).

The ability to provide a conditioning shampoo that has excellent conditioning benefits, as well as excellent foaming and stability, has been a long-felt need in the conditioning shampoo art. The conditioning shampoos of the present invention solve this long-felt need by including a polyethylenimine-silicone graft copolymer conditioning agent.

By "PEI-silicone graft copolymer," it is meant that a PEI can be grafted onto a silicone polymer backbone, or a silicone polymer can be grafted onto a PEI backbone. In either case, the PEI-silicone graft copolymer contains a polymeric PEI segment covalently bonded to a polymeric silicone segment. In one embodiment, the PEI-silicone graft copolymer can be described as a linear or branched PEI polymer having one or more pendant polymeric silicone moieties covalently bonded to the PEI backbone. In another embodiment, the PEI-silicone graft copolymer can be described as a linear or branched silicone polymer having one or more pendent PEI moieties covalently bonded to the silicone polymer backbone. Preferably, the PEI or silicone polymer backbone is linear, and the silicone polymer is an organosiloxane.

The polyethylenimine portion of the PEI-silicone graft copolymer of the conditioning shampoo of the present invention generally has the formula $(CH_2CH_2NH)_n$, wherein n is about 5 to about 2500. The integer n corresponds to the average value of repeating ethylenimine units in the preceding formula. Specific, nonlimiting examples of polyethylenimines are PEI-7 (n=7); PEI-15 (n=15); PEI-30 (n=30); PEI-45 (n=45); PEI-275 (n=275); PEI-700 (n=700); PEI-1000 (n=1000); PEI-1400 (n=1400); PEI-1500 (n=1500); PEI-1750 (n=1750); and PEI-2500 (n=2500). The PEI can be the backbone or the pendant moieties of the graft copolymer. The amount of PEI in the PEI-silicone graft copolymers is about 20% to about 95% by weight of the PEI-silicone graft copolymer, and preferably is about 30% to about 90% by weight of the graft copolymer.

The PEI in the PEI-silicone graft copolymer preferably is linear, however, the PEI also can be a branched polyethylenimine having the following general structural formula:

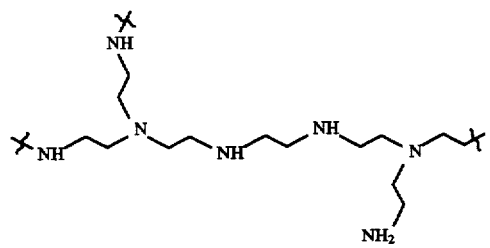

The molecular weight of the polyethylenimine grafted onto the silicone polymer backbone is not critical as long as the PEI contains about five or more repeating ethylenimine units, e.g., polyethylenimines having a weight average molecular weight of about 300 to about 70,000. The preferred polyethylenimines have a molecular weight in the range of about 700 to about 70,000. Preferred branched polyethylenimines have a ratio of primary:secondary:tertiary nitrogen atoms of about 1:2:1, respectively.

The silicone polymer portion in the PEI-silicone graft copolymer generally is an organosiloxane having the structure

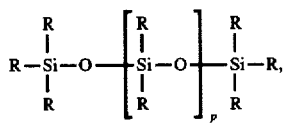

wherein R is an alkyl group having one to four carbon atoms, hydro, phenyl, hydroxy, vinyl, or a mixture thereof, and p is about 10 to about 5000. Typically, R is methyl, hydro, hydroxy, phenyl, vinyl, or a mixture thereof. Specific examples of silicone polymers are dimethylpolysiloxanes, diphenylpolysiloxanes, methylphenylpolysiloxanes, and mixtures thereof. The following are further nonlimiting examples of other useful organosiloxanes:

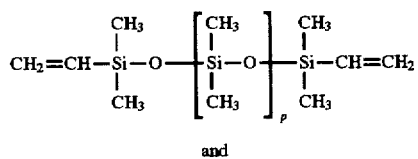

and

-continued

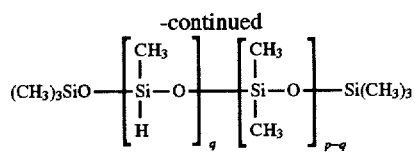

wherein q is 1 through p. The organosiloxanes have a viscosity of about 1 to about 250,000 centistokes (cs) at 25° C. The silicone polymer can be the backbone or the pendant moieties of the graft copolymer.

One class of PEI-silicone graft copolymers useful in the present invention has the general molecular formula (I):

$$H_2N(CH_2CH_2NH)_a(CH_2CH_2-N)_bCH_2CH_2NH_2, \quad (I)$$
$$\mid$$
$$X$$

wherein a is about 3 to about 2000, b is about 2 to about 1000, a+b is about 5 to about 2500, the ratio a:b is about 1.5:1 to about 20:1,

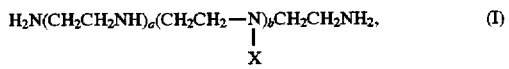

wherein c is about 10 to about 5000 and Y is methyl (—$CH_3$), vinyl (—$CH=CH_2$), or phenyl (—$C_6H_5$).

A particularly useful class of PEI-silicone graft copolymers useful in the present invention is depicted in general molecular formula (II):

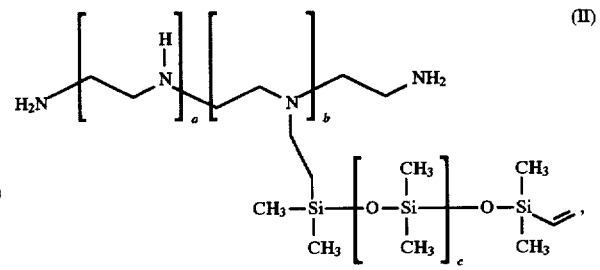

wherein a is about 15 to about 1500, and preferably about 45 to about 1500; b is about 10 to about 700, and preferably about 50 to about 500; c is about 10 to about 2500, and preferably about 50 to about 1000; and the ratio a:b is about 2:1 to about 15:1, and preferably about 3:1 to about 10:1.

The PEI-silicone graft copolymers of molecular formulae (I) and (II) are prepared by reacting a PEI of desired molecular weight (i.e., having an n of about 5 to about 2500) with an organofunctional silicone polymer to graft the PEI to the silicone polymer. The silicone fluid contains at least one functional group capable of reacting with the hydrogen atoms of an amino group in PEI. Such groups are known to persons skilled in the art and include, for example, hydroxyl, carboxyl, hydro, chloro, amino, and vinyl. An excess number of equivalents of PEI are used for each equivalent of reactive functional group on the organofunctional silicone polymer, thereby ensuring that only a minor portion of the amino functionality of the PEI reacts with the organofunctional silicone. A substantial amount of secondary amino groups of the PEI remain unreacted to maintain the cationic character of the PEI-silicone graft copolymer. Accordingly, about 1.5 to about 20 equivalents of PEI are used for each equivalent of functional group on the silicone polymer. Preferably, about 2 to about 15 equivalents, and most preferably about 3 to about 10 equivalents, of PEI are used for each equivalent of functional group.

A particular PEI-silicone graft copolymer having the general structural formula (II) is MACKAMER™ BW-147, available from MacIntyre Group Ltd., University Park, Ill. MACKAMER™ BW-147 is prepared from a PEI having a molecular weight of about 70,000 Daltons and an organo-functional silicone polymer having a molecular weight of about 60,000 Daltons, wherein about 5 equivalents of PEI are present for each equivalent of functional group on the silicone. MACKAMER™ BW-147 has the structural formula (III):

wherein r and s, independently, are integers from 1 to about 2000, and r+s is about 10 to about 3000. Other silicone compounds having a functionality that can react with ethylenimine or a PEI to provide a PEI-silicone graft copolymer useful in the present shampoo conditioner can be found in SILICON COMPOUNDS, Petrarch Systems, Bristol, Pa.

Another useful class of PEI-silicone graft copolymers have the molecular formula (IV):

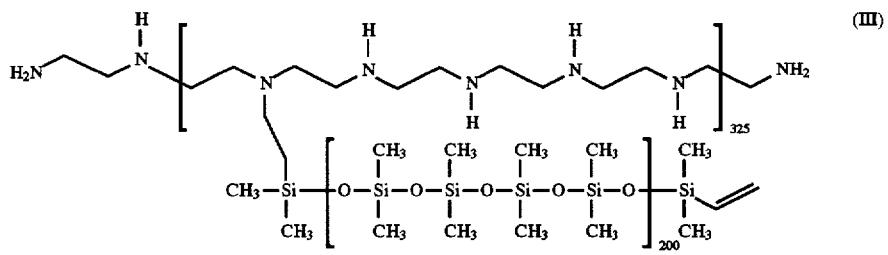

Structural formula (III) is equivalent to structural formula (I) wherein a is 1300, b is 325, a+b is 1625, the ratio a:b is 4:1, c is 800, and Y is vinyl.

Other PEI-silicone graft copolymers also are envisioned for use in the present conditioning shampoo. For example, the reaction product of an amine-functionalized organosiloxane, or a vinyl-functionalized organosiloxane, and ethylenimine provides a useful PEI-silicone graft copolymer. In addition, a functionalized silicone copolymer of desired molecular weight can be reacted with a sufficient amount of ethylenimine to provide a PEI-silicone graft copolymer having the desired amount of grafted PEI. Non-limiting examples of an amine-functionalized silicones useful in a reaction with ethylenimine to provide a graft copolymer are trimethylsilylamodimethicone and amodimethicone.

In addition to an amine functionalized silicone, a silanol can be reacted with ethylenimine to provide the PEI-silicone graft copolymer. Silanols have a reactive hydroxyl group that reacts with ethylenimine and grafts the ethylenimine onto the silicone in the form of PEI. Exemplary silanols are dimethiconol, which has a terminal hydroxyl group, and dimethicone copolyol, which has ethylene oxide side chains.

Another useful PEI-silicone graft copolymer would be the nitrogen analogue of dimethicone copolyol. This PEI-silicone graft copolymer is similar to dimethicone copolyol except the polyethylene glycol and polypropylene glycol side chains are replaced by PEI.

Another exemplary compound that can be reacted with ethylenimine to provide a PEI-silicone graft copolymer is a glycidoxypropyl methyldimethyl siloxane copolymer having the molecular formula:

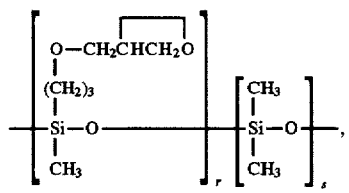

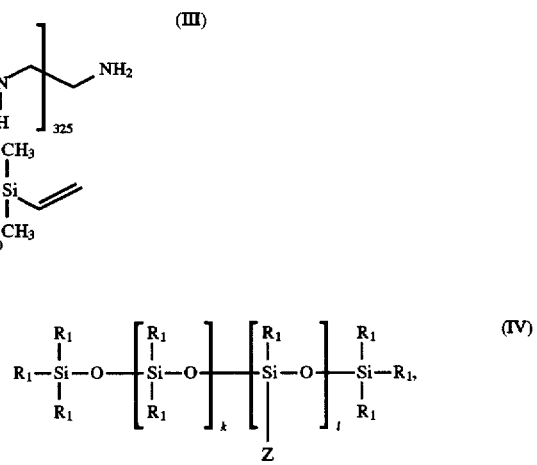

wherein $R_1$ is a hydrocarbyl group containing 1 to 6 carbon atoms, preferably methyl, phenyl, vinyl, or a mixture thereof; k is about 30 to about 3000; l is about 20 to about 2000, k+l is about 50 to about 5000; the ratio k:l is about 1.5:1 to about 20:1 and Z is —$CH_2CH_2(NHCH_2CH_2)$ $_w$$NHCH_2CH_2NH_2$, wherein w is about 5 to about 2500. The PEI-silicone graft copolymers of molecular formula (IV) are prepared in an analogous manner to the copolymers of molecular formula (I) and (II), described above.

To achieve the full advantage of the present invention, an optional foam booster, in an amount of 0% to about 20% by weight of the composition, is included in the composition to aid in the formation of copious amounts of foam. Suitable foam boosters include one or more of the following:

| | |
|---|---|
| Capramide DEA | Disodium Isostearyl Sulfosuccinate |
| Cocamide | Hydrogenated Tallow Amine Oxide |
| Cocamide DEA | Hydroxyethyl Hydroxypropyl $C_{12}$–$C_{15}$ Alkoxypropylamine Oxide |
| Cocamide MEA | Hydroxyethyl Stearamide-MIPA |
| Cocamide MIPA | Isostearamidopropylamine Oxide |
| Cocamidopropylamine Oxide | Isostearamidopopropyl Morpholine Oxide |
| Cocamine Oxide | Lauramide |
| Cocoamphodipropionic Acid | Lauramide DEA |
| Coco-Morpholine Oxide | Lauramide MEA |
| Cocoyl Hydroxyethyl Imidazoline | Lauramide MIPA |
| Cocoyl Sarcosinamide DEA | Lauramidopropylamine Oxide |
| DEA-Cocoamphodipropionate | Lauramine Oxide |
| DEA-Lauraminopropionate | Lauramine Oxide |
| DEA-Lauraminopropionate | Myristamide DEA |
| Decylamine Oxide | Myristamide MEA |
| Dihydroxyethyl $C_8$–$C_{10}$ Alkoxypropylamine Oxide | Myristamide MIPA |
| Dihydroxyethyl $C_9$–$C_{11}$ Alkoxypropylamine Oxide | Myristamidopropylamine Oxide |

| | |
|---|---|
| Dihydroxyethyl $C_{12}$–$C_{15}$ Alkoxy-propylamine Oxide | Myristamine Oxide |
| Dihydroxyethyl Cocamine Oxide | Myristaminopropionic Acid |
| Dihydroxyethyl Stearamine Oxide | Oleamidopropylamine Oxide |
| Dihydroxyethyl Tallowamine Oxide | Oleamine Oxide |
| Palmamide MEA | Palmamide DEA |
| Palmamide MIPA | PEG-5 Lauramide |
| Palmitamide DEA | PEG-6 Lauramide |
| Palmitamide MEA | PEG-3 Lauramine Oxide |
| Palmitamidopropylamine Oxide | Sodium Cocoamphoacetate |
| Palmitamine Oxide | Sodium Cocoamphopropionate |
| Palm Kernelamide DEA | Sodium Lauraminopropionate |
| Palm Kernelamide MEA | Sodium Lauroamphopropionate |
| Palm Kernelamide MIPA | Sodium Lauroyl Sarcosinate |
| Peanutamide MEA | Sodium Myristoamphoacetate |
| Peanutamide MIPA | Sodium Myristoyl Sarcosinate |
| PEG-6 Cocamide | TEA-Hydrogenated Tallow Glutamate |
| PEG-3 Lauramide | TEA-Lauraminopropionate |
| Undecylenamidopropylamine Oxide | TEA-Myristaminopropionate |
| Undecylenamide MEA | Undecylenamide DEA |

Other alkanolamides, amine oxides, sulfosuccinates, alkamphopropionates, alkaminopropionates, imidazolines, alkamphoacetates, and alkoyl sarcosinates, are listed in McCutcheon's Detergents and Emulsifiers, 1989 Annual, published by McCutcheon Division, MC Publishing Co., incorporated herein by reference.

One or more optional zwitterionic detergents, such as a betaine and/or sultaine, in an amount of 0% to about 10% by total weight of the composition, aids in foam generation and conditioning the hair. Nonlimiting betaines and sultaines include, for example:

| | |
|---|---|
| Betaine | Myristamidopropyl Betaine |
| Cetyl Betaine | Myristyl Betaine |
| Cocamidoethyl Betaine | Oleamidopropyl Betaine |
| Cocamidopropyl Betaine | Oleamidopropyl Hydroxysultaine |
| Cocamidopropyl Hydroxysultaine | Oleyl Betaine |
| Coco-Betaine | Palmamidopropyl Betaine |
| Coco/Oleamidopropyl Betaine | Palmitamidopropyl Betaine |
| Coco-Sultaine | Ricinoleadmidopropyl Betaine |
| Decyl Betaine | Stearamidopropyl Betaine |
| Hydrogenated Tallow Betaine | Stearyl Betaine |
| Isostearamidopropyl Betaine | Tallowamidopropyl Betaine |
| Lauramidopropyl Betaine | Tallowamindopropyl Hydroxysultaine |
| Lauryl Betaine | Wheat Germamidopropyl Betaine |
| Lauryl Sultaine | |

Other compounds useful for additional composition stabilization, in an amount of about 0.1% to about 10% by total weight of the composition, include, for example, one or more of the following:

| | |
|---|---|
| Acetylated Glycol Stearate | Maltodextrin |
| Aluminum Caprylate | Methoxy PEG-22/Dodecyl Glycol Copolymer |
| Aluminum Dilinoleate | Microcrystalline Cellulose |
| Aluminum Distearate | Myristyl Alcohol |
| Aluminum Isostearates/Laurates/Palmitates | Pectin |
| Aluminum Isostearates/Laurates/Stearates | PEG-2M |
| Aluminum Isostearates/Myristates | PEG-5M |
| Aluminum Isostearates/Palmitates | PEG-7M |
| Aluminum Isostearates/Stearates | PEG-9M |
| Aluminum Lanolate | PEG-14M |
| Aluminum Myristates/Palmitates | PEG-20M |
| Aluminum Stearate | PEG-23M |
| Aluminum Tristearate | PEG-45M |
| $C_9$–$C_{11}$ Alcohols | PEG-90M |
| $C_{12}$–$C_{13}$ Alcohols | PEG-115M |
| $C_{12}$–$C_{15}$ Alcohols | PEG-22/Dodecyl Glycol Copolymer |
| $C_{12}$–$C_{16}$ Alcohols | PEG-45/Dodecyl Glycol Copolymer |
| $C_{14}$–$C_{15}$ Alcohols | Polyvinyl Acetate |
| $C_{15}$–$C_{18}$ Glycol | PVM/MA Copolymer |
| Carboxymethyl Hydroxypropyl Guar | PVP/VA Copolymer |
| Ceresin | Sodium Acrylate/Vinyl Alcohol Copolymer |
| Cetearyl Alcohol | Sodium $C_4$–$C_{12}$ Olefin/Maleic Acid Copolymer |
| Cetyl Alcohol | Sodium Carboxymethyl Dextran |
| Coconut Alcohol | Sodium Cellulose Sulfate |
| Ethylene/Acrylate Copolymer | Sodium Polynaphthalene Sulfonate |
| Ethylene/Vinyl Acetate Copolymer | Sodium Polystyrene Sulfonate |
| Isopropyl Ester of PVM/MA Copolymer | Stearyl Alcohol |
| Lanolin | Stearylvinyl Ether/Maleic Anhydride Copolymer |
| Lanolin Alcohol | Styrene/Maleic Anhydride Copolymer |
| Lauryl Alcohol | Tallow Alcohol |
| Locust Bean Gum | Distearyl amate (distearyl phthalamic acid) |
| | Tridecyl Alcohol |

In accordance with an important feature of the present invention, such stabilizers are not necessary ingredients in the conditioning shampoos. The PEI-silicone graft copolymer imparts sufficient stability to the composition. However, including an optional stabilizer in the composition does not adversely affect the composition, and can impart additional esthetic properties to the composition. In preferred embodiments, the conditioning shampoo is free of a stabilizing agent.

The conditioning shampoos of the present invention also can be thickened, for example, with sodium alginate, guar gum, xanthan gum, gum arabic, karaya gum, carrageenan, calcium carrageenan, potassium carrageenan, potassium alginate, tragacanth gum, cellulose gum, cellulose derivatives such as methylcellulose, hydroxyethylcellulose, hydroxypropylmethylcellulose and carboxymethylcellulose; and various polymeric thickeners, such as polyacrylic acid derivatives. These thickeners are present in an amount of 0% to about 5%, and preferably from about 0.14% to about 1%, by total weight of the composition. Such optional thickeners increase the viscosity of the composition to provide a desired esthetic effect.

Other common cosmetic components and additives that can be incorporated into the conditioning shampoos of the present invention, as long as the basic properties of conditioning, cleansing and high foam levels are not adversely affected include, for example, fragrances, dyes, hair colorants, opacifiers, pearlescing agents, dandruff control agents, hydrotropes, foam stabilizers, solubilizers, preservatives, water softening agents, acids, bases, buffers and the like. These optional components and additives are common in the art, and usually are present in amounts of less than about 2% each, and from about 5% to about 10%, by total weight of the composition.

The conditioning shampoos also can include other emulsifiers, inorganic salts, humectants and similar materials to impart esthetic properties and desirable physical properties to the composition. Generally, such optional ingredients are present in weight percentages ranging from about 0% to about 10% each, and from about 0.1% to about 20% in total, relative to the total weight of the composition.

The vehicle of the conditioning shampoo composition is predominantly water, but organic solvents also can be used in order to help solubilize compounds that are not sufficiently soluble in water. Suitable solvents include the lower alcohols like ethyl alcohol and isopropyl alcohol; polyols like glycerol; glycols or glycol ethers, like 2-butoxyethanol, ethylene glycol, ethylene glycol monoethyl ether, propylene glycol and diethylene glycol monoethyl ether or monoethyl ether; and mixtures thereof. These organic solvents can be present in the hair-treating composition of the present invention in an amount from about 1% to 50% by weight and, in particular, from about 2% to about 25% by weight, relative to the total weight of the vehicle in the composition.

The compositions of the present invention are relatively viscous dispersions or emulsions that are stable to phase separation at a temperature of about 20° C. to about 25° C. for at least 24 hours after preparation, and typically are stable to phase separation indefinitely at such temperatures. The conditioning shampoos demonstrate sufficient stability to phase separation at temperatures normally found in commercial product storage and shipping to remain unaffected for period of one year or more.

The following examples illustrate various conditioning shampoos made in accordance with the present invention:

EXAMPLES 1-4

| EXAMPLE | 1 wt. % | 2 wt. % | 3 wt. % | 4 wt. % |
|---|---|---|---|---|
| 1. Water | 57.10 | 56.60 | 55.60 | 47.60 |
| 2. Methocel 40-101 (hydroxypropyl methylcellulose) (viscosity increasing agent) | 0.35 | 0.35 | 0.35 | 0.35 |
| 3. Ammonium Lauryl Sulfate (anionic surfactant) | 35.00 | 35.00 | 35.00 | 35.00 |
| 4. MACKAMER ™ BW-147 (PEI-silicone copolymer) | 0.50 | 1.00 | 2.00 | 10.00 |
| 5. Cocamide DEA (foam booster) | 3.00 | 3.00 | 3.00 | 3.00 |
| 6. Glydant (preservative) | 0.25 | 0.25 | 0.25 | 0.25 |
| 7. KATHON CG (preservative) | 0.05 | 0.05 | 0.05 | 0.05 |
| 8. Perfume (fragrance) | 0.50 | 0.50 | 0.50 | 0.50 |
| 9. Cold Pearl Mix | 2.00 | 2.00 | 2.00 | 2.00 |
|   sodium lauryl sulfate (30% active) 1.32% | | | | |
|   propylene glycol 0.20% | | | | |
|   cocamide DEA 0.04% | | | | |
|   ethylene glycol monostearate 0.40% | | | | |
|   cetyl palmitate 0.04% | | | | |
|   Total 2.00% | | | | |
| 10. Ammonium chloride (viscosity adjustment) | 1.25 | 1.25 | 1.25 | 1.25 |
| | 100.00 | 100.00 | 100.00 | 100.00 |
| | pH 8.50 | pH 8.8 | pH 8.9 | pH 9.0 |
| Add liquid citric acid (50%) (pH adjustment) | 0.20 | 0.20 | 0.25 | 0.25 |
| Final pH: | 6.50 | 6.60 | 6.50 | 6.60 |
| Viscosity: | 4,200 cps | 4,000 cps | 4,000 cps | 4,000 cps |

Mixing Procedure Examples 1-4:

Disperse Methocel (#2) in water and mix for 25 minutes. Than add ALS (#3) and mix for 5 minutes. Add MACKAMER® BW-147 (#4), continue mixing for ½ hour. Then add the remaining ingredients (#5-10) with mixing.

The compositions of Examples 1-4 did not contain a stabilizer and were phase stable compositions. The compositions of Examples 1-4 generated a consumer acceptable foam level and effectively cleansed and conditioned the hair.

EXAMPLE 5

| | wt. % |
|---|---|
| 1. Water, Soft | 37.478 |
| 2. Liquid Citric Acid (50%) (pH adjustment) | 0.010 |
| 3. Methocel 40-100 (hydroxypropyl methylcellulose) (viscosity increasing agent) | 0.150 |
| 4. Water, soft | 2.000 |
| 5. VERSENE ® 100 | 0.200 |
| 6. Liquid Citric Acid (pH adjustment) | 0.160 |
| 7. DMDM Hydantoin (preservative) | 0.100 |
| 8. KATHON CG (preservative) | 0.050 |
| 9. IGEPAL ® CA 630 ($C_8H_{17}C_6H_4(OCH_2CH_2)_9OH$) (solubilizer) | 0.750 |
| 10. SILWET ® L720 (silicone copolymer) (conditioner) | 0.001 |
| 11. Sodium Lauroyl Sarcosinate (amphoteric surfactant) | 1.000 |
| 12. Propylene glycol (moisturizer) | 0.500 |
| 13. PPG-30 cetyl ether (emollients) | 0.001 |
| 14. Fragrance | 0.600 |
| 15. Dynol ALS (anionic surfactant) | 21.00 |
| 16. Surfactant Blend: | 30.00 |
|   (a) ALES (1 mole ethoxylation) (4.5%) | |
|   (b) lauramide DEA (2.5%) | |
|   (c) ammonium xylene sulfonate (0.6%) | |
|   (d) water q.s. | |
| 17. Tegobetaine L7 (amphoteric surfactant) | 3.00 |
| 18. MACKAMER ™ BW-147 (PEI-silicone copolymer) | 2.00 |
| pH | 6.45 |
| viscosity | 6,000 cps |

Mixing Procedure Example 5:

Add the Liquid Citric Acid (50%) (#2) to water (#1).
Add Methocel (#3) to the batch with high agitation for 20 minutes or mix until free of lumps.
Add #4, soft water.
Add #5, VERSENE® 100.
Add #6, Liquid Citric Acid.
Add #7, DMDM hydantoin.
Add #8, KATHON CG.
Add #9, IGEPAL® CA 630.
Add #10, SILWET® L720.
Add #11, Sodium Lauryl Sarcosinate.
Add #12, Propylene Glycol.
Add #13, Wickenol 707.
Add #14, Fragrance.
Add #15, Dynol ALS.
Add #16, Surfactant Blend.
Add #17, Tegobetaine L7.
Add #18, MACKAMER™ BW-147.
Mix the batch for one (1) hour at room temperature 20°-25° C.

The composition of Example 5 did not contain a stabilizer and was a phase stable composition. The composition of Example 5 generated an excellent foam level and effectively cleansed and conditioned the hair.

What is claimed is:

1. A conditioning shampoo for thoroughly cleansing and conditioning hair while maintaining foam comprising, by total weight of the conditioning shampoo:
   (a) about 10% to about 90% water;
   (b) about 5% to about 65% of an anionic surfactant; and
   (c) about 0.01% to about 20% of a polyethylenimine-silicone graft copolymer containing repeating units of $(CH_2CH_2NH)_n$, wherein n is about 5 to about 2500.

2. The conditioning shampoo of claim 1 wherein the conditioning shampoo comprises about 5% to less than about 15% of the anionic surfactant, by total weight of the conditioning shampoo.

3. The conditioning shampoo of claim 1 wherein the anionic surfactant is selected from the group consisting of a long chain ($C_{12}$–$C_{22}$) alkyl sulfate, a long chain ($C_{12}$–$C_{22}$) alkyl ether sulfate, a long chain ($C_{12}$–$C_{22}$) alkyl sulfonate, a long chain ($C_{12}$–$C_{22}$) alkyl ether carboxylate, a long chain ($C_{12}$–$C_{22}$) alkyl ether sulfonate, and mixtures thereof.

4. The conditioning shampoo of claim 1 further comprising 0% to about 20%, based on the total weight of the conditioning shampoo, of a foam booster selected from the group consisting of an alkanolamide, an amine oxide, a sulfosuccinate, an alkamphopropionate, an alkamphodipropionate, an alkaminopropionate, an imidazoline, an alkamphoacetate, an alkoyl sarcosinate, and mixtures thereof.

5. The conditioning shampoo of claim 1 wherein the conditioning shampoo further includes 0% to about 5% by total weight of the composition, of a thickener, said conditioning shampoo having a viscosity of at least about 3,000 centipoises.

6. The conditioning shampoo of claim 1 further comprising a zwitterionic detergent in an amount of 0% to about 10%, by total weight of the conditioning shampoo.

7. The conditioning shampoo of claim 6 wherein the zwitterionic detergent is a betaine, a sultaine, or a mixture thereof.

8. The conditioning shampoo of claim 1 having a pH of about 4.5 to about 7.5.

9. The conditioning shampoo of claim 1 wherein the graft copolymer has polyethylenimine pendant moieties grafted onto a silicone polymer backbone.

10. The conditioning shampoo of claim 1 wherein the graft copolymer has silicon polymer pendant moieties grafted onto a polyethylenimine backbone.

11. The conditioning shampoo of claim 1 wherein the polyethylenimine and the silicone polymer each is a linear polymer and are covalently bonded to one another.

12. The conditioning shampoo of claim 1 wherein n is about 15 to about 1500.

13. The conditioning shampoo of claim 1 wherein n is about 30 to about 1000.

14. The conditioning shampoo of claim 1 wherein the polyethylenimine portion of the graft copolymer has a weight average molecular weight of about 700 to about 70,000.

15. The conditioning shampoo of claim 1 wherein the polyethylenimine is branched and has a ratio of primary-:secondary:tertiary nitrogen atoms of about 1:2:1.

16. The conditioning shampoo of claim 1 wherein the polyethylenimine-silicone graft copolymer contains about 20% to about 95%, by weight of the graft copolymer, of polyethylenimine.

17. The conditioning shampoo of claim 1 wherein the silicone portion of the graft copolymer is an organosiloxane having the structure:

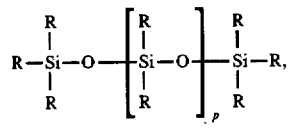

wherein R is selected from the group consisting of an alkyl group having one to four carbon atoms, hydro, hydroxy, phenyl, vinyl, and mixtures thereof, and p is about 10 to about 5000.

18. The conditioning shampoo of claim 17 wherein R is selected from the group consisting of methyl, hydro, hydroxy, phenyl, vinyl, and mixtures thereof, and the organosiloxane has a viscosity of about 1 to about 250,000 centistokes at 25° C.

19. The conditioning shampoo of claim 17 wherein the organosiloxane has the structure:

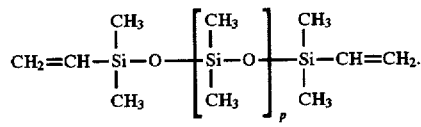

20. The conditioning shampoo of claim 17 wherein the organosiloxane has the structure:

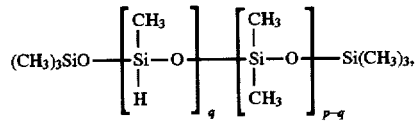

wherein q is 1 through p.

21. The conditioning shampoo of claim 1 wherein the polyethylenimine-silicone graft copolymer has the molecular formula:

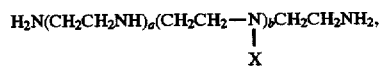

wherein a is about 3 to about 2000, b is about 2 to about 1000, a+b is about 5 to about 2500, ratio a:b is about 1.5:1 to about 20:1,

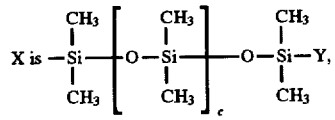

wherein c is about 10 to about 5000, and Y is methyl, vinyl, or phenyl.

22. The conditioning shampoo of claim 1 wherein the polyethylenimine-silicone graft copolymer has the molecular formula:

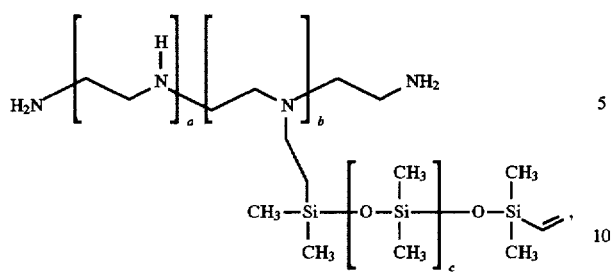

wherein a is about 15 to about 1500, b is about 10 to about 700, c is about 10 to about 2500, and a:b is about 2:1 to about 15:1.

23. The conditioning shampoo of claim 22 wherein a is about 45 to about 1500, b is about 50 to about 500; c is about 50 to about 1000, and a:b is about 3:1 to about 10:1.

24. The conditioning shampoo of claim 22 having the molecular formula:

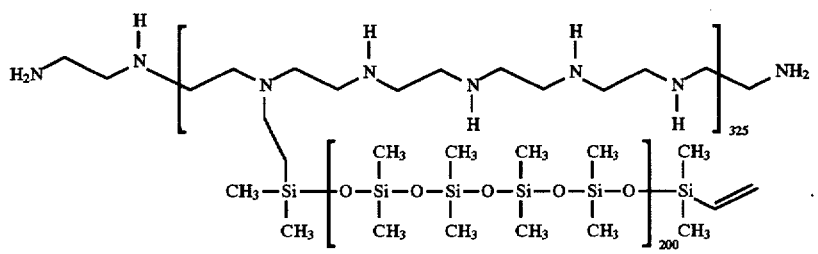

25. The conditioning shampoo of claim 1 wherein the polyethylenimine-silicone graft copolymer is a reaction product of an amine-functionalized organosiloxane and ethylenimine.

26. The conditioning shampoo of claim 1 wherein the polyethylenimine-silicone graft copolymer is a reaction product of a vinyl-functionalized organosiloxane and ethylenimine.

27. The conditioning shampoo of claim 1 wherein the polyethylenimine-silicone graft copolymer is a reaction product of dimethicone and ethylenimine.

28. The conditioning shampoo of claim 1 wherein the polyethylenimine-silicone graft copolymer is a reaction product of dimethicone copolyol and ethylenimine.

29. The conditioning shampoo of claim 1 wherein the polyethylenimine-silicone graft copolymer is a reaction product of ethylenimine and a glycidoxypropyl methyldimethyl siloxane copolymer having the molecular formula:

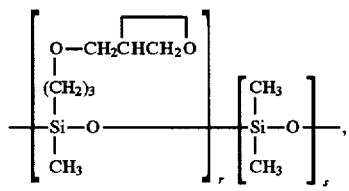

wherein r and s, independently, are integers from 1 to about 2000, and r+s is about 10 to about 3000.

30. The conditioning shampoo of claim 1 wherein the polyethylenimine- silicone graft copolymer has the molecular formula:

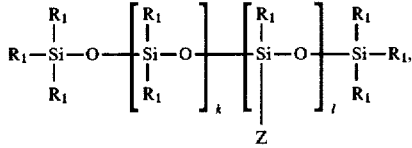

wherein $R_1$ is a hydrocarbyl group containing 1 to 6 carbon atoms, k is about 30 to about 3000, l is about 20 to about 2000, k+l is about 50 to about 5000, k:l is about 1.5:1 to about 20:1, and Z is $—CH_2CH_2(NHCH_2CH_2)_w NHCH_2CH_2NH_2$, wherein w is about 5 to about 2500.

31. The conditioning shampoo of claim 1 wherein the conditioning shampoo is free of a stabilizer.

32. The conditioning shampoo of claim 30 wherein $R_1$ is selected from the group consisting of methyl, phenyl, vinyl, and mixtures thereof.

33. A conditioning shampoo for thoroughly cleansing and conditioning hair while maintaining foam comprising, by the total weight of the conditioning shampoo:

(a) about 10% to about 80% water;

(b) about 5% to about 25% of an anionic surfactant; and (c) about 0.05% to about 10% of a polyethylenimine-organosiloxane graft copolymer containing repeating units of $(CH_2CH_2NH)_n$, wherein n is about 30 to about 1000.

34. A method of cleansing and conditioning hair, simultaneously, while maintaining a substantial quantity of foam and excellent cleansing using a conditioning shampoo comprising:

(a) contacting the hair with the conditioning shampoo comprising, by total weight of the conditioning shampoo:

(i) about 10% to about 90% water;

(ii) about 5% to about 65% of an anionic surfactant; and (iii) about 0.01% to about 20% of a polyethylenimine-silicone graft copolymer having repeating $(CH_2CH_2NH)_n$ units, wherein n is about 5 to about 2500; and (b) rinsing the conditioning shampoo from the hair.

* * * * *